(12) United States Patent
Castillo et al.

(10) Patent No.: US 6,486,208 B1
(45) Date of Patent: Nov. 26, 2002

(54) SUSTAINED RELEASE, AND COMFORTABLE OPTHALMIC COMPOSITION AND METHOD FOR OCULAR THERAPY

(75) Inventors: Ernesto J. Castillo, Arlington; Ruma Sarkar, Fort Worth; Onkar N. Singh, Arlington; Alan L. Weiner, Arlington, all of TX (US); Cody Yarborough, Fort Collings, CO (US)

(73) Assignee: Alcon Laboratories, Inc., Fort Worth, TX (US)

( * ) Notice: Subject to any disclaimer, the term of this patent is extended or adjusted under 35 U.S.C. 154(b) by 0 days.

(21) Appl. No.: 09/787,203
(22) PCT Filed: Sep. 22, 1999
(86) PCT No.: PCT/US99/21957
§ 371 (c)(1), (2), (4) Date: Mar. 15, 2001
(87) PCT Pub. No.: WO00/18316

PCT Pub. Date: Apr. 6, 2000

Related U.S. Application Data

(60) Provisional application No. 60/101,959, filed on Sep. 25, 1998.

(51) Int. Cl.$^7$ ............................................. A61K 31/135
(52) U.S. Cl. ....................... 514/646; 514/652; 514/912
(58) Field of Search ................................. 514/646, 652, 514/912

(56) References Cited

U.S. PATENT DOCUMENTS 4,911,920 A    3/1990   Jani et al.

*Primary Examiner*—Zohreh Fay
(74) *Attorney, Agent, or Firm*—McDermott, Will & Emery

(57) ABSTRACT

This invention relates to reduced stinging, sustained release ophthalmic formulations and the method of treatment comprising administering such formulations topically to the eye when in need thereof.

33 Claims, No Drawings

SUSTAINED RELEASE, AND COMFORTABLE OPTHALMIC COMPOSITION AND METHOD FOR OCULAR THERAPY

This application claim the benefit of U.S. provisional application Ser. No. 60/101,959, filed Sep. 25, 1998

TECHNICAL FIELD

The present invention relates to improved nonstinging, sustained release ophthalmic formulations for ocular therapy and methods of treatment comprising administering such formulations topically to the eye when indicated.

BACKGROUND ART

Numerous drugs are not readily accepted by many patients because they cause ocular discomfort, i.e., "stinging," upon instillation to the eyes. This side effect is problematic because it results in poor patient compliance and because it restricts the amount of drug which can be included in topical formulations. Further, to meet USP and global microbiological standards, one or more preservatives must be included in ocular formulations. These preservatives, particularly those required to meet more stringent global requirements, have the tendency to increase the level of "stinging", thereby augmenting patient discomfort. Thus, the combined requirements of comfort and satisfactory patient compliance together with provision of a composition which meets stringent global preservative requirements pose a challenge which, to date, has not been satisfactorily achieved.

One method for addressing the problems associated with the topical administration is described in U.S. Pat. No. 4,911,920. Glaucoma is a disease characterized by an elevated intraocular pressure (IOP) associated with optic nerve head damage and loss of visual field. Statistically, when IOP is lowered, the prognosis for preserving visual field in an eye with elevated IOP is improved. Thus, a goal of glaucoma therapy is to reduce the IOP to a level within a range tolerated by the eye to slow the progressive loss of visual field. Current medical therapy of glaucoma involves the reduction of IOP by various drugs, predominantly ophthalmic beta adrenergic blocking drugs. Betaxolol is among the ophthalmic beta blockers approved for use to treat glaucoma in the United States. In the '920 patent, actives such as betaxolol are administered to treat glaucoma in a composition which includes, inter alia, an ion exchange resin and a polyanionic polymer. These compositions have an excellent comfort profile but "stinging" is still experienced by some patients.

Thus, there exists a need to provide an ophthalmic composition which achieves the combined requirements of comfort and satisfactory patient compliance, while, at the same time, meets stringent global preservative requirements.

DISCLOSURE OF THE INVENTION

An advantage of the present invention is that it achieves the combined requirements of comfort and satisfactory patient compliance, while, at the same time, meets stringent global preservative requirements, thereby permitting the topical administration of ophthalmic drugs and in higher concentrations.

Additional advantages and other features of the present invention will be set forth in part in the description which follows and in part will become apparent to those having ordinary skill in the art upon examination of the following or may be learned from the practice of the invention. The objects and advantages of the invention may be realized and obtained as particularly pointed out in the appended claims.

According to the present invention, the foregoing and other advantages are achieved in part by an ophthalmic composition, comprising: a) at least one basic active; b) a polyanionic polymer; c) an ion exchange resin; and d) a pH adjusting agent, wherein said agent is present in an amount sufficient to adjust the pH of the composition to between about 3.5 and 9.5.

Another aspect of the present invention is a method of treatment which comprises administering topically to an affected eye, an ophthalmic composition comprising: a) at least one basic active; b) a polyanionic polymer; c) an ion exchange resin; and d) a pH adjusting agent, wherein said agent is present in an amount sufficient to adjust the pH of the composition to between about 3.5 and about 9.5.

Additional objects and advantages of the present invention will become readily apparent to those skilled in this art from the following detailed description, wherein only the preferred embodiment of the invention is, shown and described, simply by way of illustration of the best mode contemplated for carrying out the invention. As will be realized, the invention is capable of other and different embodiments, and its several details are capable of modifications in various obvious respects, all without departing from the invention. Accordingly, the drawings and description are to be regarded as illustrative in nature, and not as restrictive.

DESCRIPTION OF THE INVENTION

The present invention is based, in part, on the surprising and unexpected discovery that the use of certain pH adjusting agents, result in ophthalmic compositions which achieve the combined requirements of comfort and satisfactory patient compliance, while, at the same time, meets stringent global preservative requirements.

The pH adjusting agents useful in the present invention may be any "basic amine", i.e., any amine which shows basicity and does not substantially disrupt interaction between a basic active and an ion exchange resin. Preferred pH adjusting agents include ammonia, tromethamine (TRIS or Tris(hydroxymethyl) aminomethane), triethanolamine (TEA), N-2-hydroxyethylpiperazine-N'-2-ethanesulfonic acid (HEPES), and mixtures thereof Disruptions between a basic active and an ion exchange resin normally occur when smaller ions such as sodium ions are used to adjust the pH of the compositions of concern because they sterically fit better into the resin binding site thereby displacing the basic active from the resin and increasing the concentration of "free" basic active in solution. Since ocular discomfort with many basic actives is proportional to the amount of this "free", or unassociated basic active present in the composition, the level of discomfort experienced by patients increases as the concentration of unassociated basic active increases. While not wishing to be bound by any particular theory, it is believed that the pH adjusting agents of the present invention minimize disruption of the basic active/resin interaction as the pH is adjusted which normally occurs with smaller ions such as sodium ions. It is believed that the larger ions provided by the present invention do not fit as well into the resin binding site and therefore, do not displace as many basic active molecules.

The term "basic active" as used throughout the specification means the active ingredient or ingredients in the inventive formulations which may cause ocular discomfort upon instillation to the eye and have the desired effect and which bear, or are capable of bearing a positive charge during formulation of the final product or as formulated in the final product form. Thus, the term basic, or cationic, active is descriptive for purposes of the disclosure and claims.

Such basic actives include all ophthalmic agents which can be topically applied. Such ophthalmic agents include, but are not limited to, glaucoma agents, such as beta-blockers, muscarinics, and carbonic anhydrase inhibitors; dopaminergic agonists and antagonists; α-2 agonists; anti-infectives; non-steroidal and steroidal anti-inflammatories; prostaglandins; proteins; growth factors and anti-allergics. Compositions of the present invention may also include combinations of ophthalmic agents.

A preferred basic active is beta blockers which, typically, are represented by the following generic structure, which structure also represents the beta blocker basic actives of the present invention:

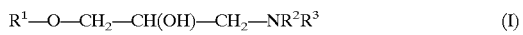

$$R^1-O-CH_2-CH(OH)-CH_2-NR^2R^3 \quad (I)$$

wherein: $R^1$ is a substituted or unsubstituted cyclic or aliphatic moiety; cyclic moieties include mono- and polycyclic structures which may contain one or more heteroatoms selected from C, N, and O; $R^2$ and $R^3$ are independently selected from H and substituted and unsubstituted alkyl. With regard to Structure (I), above, the following references are incorporated herein by reference: *Annual Reports in Medicinal Chemistry* 14, 81–87 (1979); *J. Med. Chem.* 1983, 26,1570–1576; ibid. 1984, 27, 503–509; ibid. 1983, 26, 7–11; ibid. 1983, 26, 1561–1569; ibid. 1983 1109–1112; ibid 1983, 26, 950–957; ibid. 1983, 26, 649657; and ibid 1983, 26, 352–357. Representative of such basic actives are: betaxolol, timolol, befunolol, labetalol, propranolol, bupranolol, metaprolol, bunalol, esmalol, pindolol, carteolol, hepunolol, metipranolol, celiprolol, azotinolol (S-596), diacetolol acebutolol, salbutamol, atenulol, isoxaprolol, and the like. The following patent publications, which are incorporated herein by reference, further representatively demonstrate the beta blockers of the present invention: U.S. Pat. Nos. 4,252,984; 4,311,708 and 4,342,783.

Preferred beta blockers of the present invention include betaxolol and timolol. Another preferred basic active is the (S)-isomer of betaxolol, namely, levobetaxolol, the more active of the enantiomers. The inventive formulations may comprise more than one basic active, such as levobetaxolol or betaxolol and a carbonic anhydrase inhibitor or a prostaglandin.

In the case where more than one basic active is used in the inventive formulation, the preferred basic actives include betaxolol or levobetaxolol with prostaglandin, or a prostaglandin analog, such as, but not limited to, cloprostenol or fluprostenol. More preferably, the prostaglandin includes isopropyl ester of the (+) isomer of fluprostenol (travoprost) having a formula as shown below:

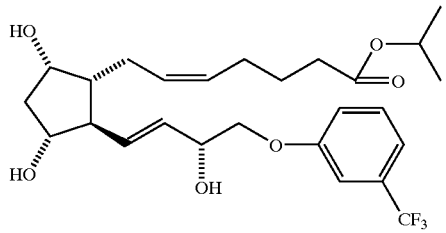

The basic active, in the gel and pourable liquid embodiments, is present at a level of from about 0.0001 to 5.0 wt. %, the most preferred range is from 0.001 to 1.0 wt. %.

As used herein, prostaglandin includes prostaglandin and prostaglandin analogs thereof, such as, but not limited to, cloprostenol and fluprostenol, as described in U.S. Pat. No. 5,510,383, which is incorporated herein by reference in its entirety to the extent that it describes the preparation and known pharmacological profiles of prostaglandin and prostaglandin analogs, especially cloprostenol, fluprostenol, latanoprost, and travoprost.

The high molecular weight, polyanionic polymers useful in the present invention have a molecular weight of from about 50,000 to about 5 billion, preferably about 700,000 to about 3 billion. The polymers are characterized as having carboxylic acid functional groups, and preferably contain from 2 to 7 carbon atoms per functional group. The gels which form during the preparation of the ophthalmic polymer dispersion have a viscosity of from about 3,000 to about 100,000 cps. In addition to the basic active-polymer (anionic-cationic) interactions, mentioned above, the high molecular weight polymers used in the compositions of the present invention thicken the compositions to provide a gel, and provide a special type of rheology, i.e., plastic viscosity, which is translatable to the sustained release and comfort of the final compositions. Such compositions range in pH from 3.0 to 8.5.

The pourable liquid embodiments (administered as drops to the eye) of the present invention have a viscosity of from about 1 to 20,000 cps. The pH requirements are the same as recited above for the gel final products, i.e., pH 3.0–8.5.

The third pharmaceutical form of the present invention, the anhydrous salt form, is derived from the free acid or the salt of the polycarboxylic acid polymer and the basic active. (The presence of the cationic ion exchange resin also contributes to salt formation; the nature of the ion exchange resin, in all embodiments of the present invention, is defined below.) Such salts can be formulated, or reconstituted, to aqueous gels and pourable dispersions, as described above, on addition of water; or can be formulated as ocular inserts according to known technology and shapes; or they can be combined with an oleaginous vehicle to form an ophthalmic ointment. All such final ophthalmic pharmaceutical forms are fully described below.

The term "plastic viscosity", above, is indicative of a material that does not perceptibly flow until a certain force or stress value is exceeded; this-force or stress is referred to as the yield value. While not wishing to be bound by any theory, it is believed that the increased duration of activity of the compositions as well as the outstanding suspension properties of the present invention are related to the polymer viscoelastic response to shear, i.e., exhibiting a definite yield value. The compositions of the present invention exhibit a unique response to shear stress. When the yield value is exceeded, the gel structure is altered temporarily, allowing the gel to flow. In the eye, this mechanism is partially attributable to the blinking eyelid. When the stress is removed (eyelid at rest), the structure of the gel is partially reestablished. Other factors which explain the duration of the formulations of the present invention are related to ionic interactions, and a release mechanism which is explained by a dynamic equilibrium involving normal tear production and the displacement of basic active cations by cations present in tears.

Suitable polyanionic polymers useful in the present invention are carboxyl vinyl polymers. Preferred polymers of this class include the so called Carbomers, available under the trade name Carbopol from the B.F. Goodrich Company; and ethylene maleic anhydride polymeric material available under the trade name EMA from the Monsanto Company. The known and readily available polymers Carbopol 974 P is specifically preferred. The polymers are used in the aqueous gel compositions at a level up to about 8% by weight; pourable liquid compositions comprise 0.05% to 2.0% by weight polymer.

The cationic resin component of the formulations of the present invention provides an additional means of sustained release of the basic active, and appears to be necessary for initial and prolonged comfort Such resins are characterized as either strongly acidic such as those having sulfonic acid functionality, or weakly acidic cation exchangers such as those having carboxylic acid functionality. The resin should be incorporated as a finely divided powder, that is, 95% of the resulting spheroidal particles should have a diameter less than 25 microns, preferably 10 or less. The release of the basic active held by the cation exchange resin and the anionic polymer is achieved when ions naturally present in the tear fluid, principally sodium and potassium, compete with the bound basic active for sites on the polymer vehicle and the ion exchange resin. Thus released, the basic active is presented to the eye surface for transport to the receptor sites.

Any pharmaceutical grade cationic ion exchange resin is suitable for the formulation, an they can be used either in the hydrogen form or in the sodium form. Such resins are readily available, for example, from Rohm & Haas under the "Amberlite" tradename and from Dow Chemical Co. under the "Dowex" tradename. A preferred ion exchange resin is Amberlite® IRP69, a cross-linked polystyrene sulfonic acid.

The ion exchange resin component is present in the formulations of the present invention at a level of from 0.05% to 10.0% by weight. The average particle size diameter of the resin ranges from 1 to 25 microns preferably 1–10.

The particle size of the resin is important, both with respect to mode of action and comfort. Typically the average particle size of the commercially available form of the ion exchange material of choice is about 40 to 150 microns. Such particles are most conveniently reduced to a particle size range of about 1.0 to 25 preferably 1–10 microns by ball milling, according to known techniques.

The pH adjusting agents are present in an amount sufficient to adjust the pH of the composition to between about 3.5 and about 9.5, preferably, between about 5 and about 9, more preferably between about 6 and 8, and most preferably to a pH of about 6.5. HCl may be optionally used to adjust the pH in conjunction with the pH adjusting agents of the present invention.

Ophthalmic products are typically packaged in unit dose (single dose) or multidose form. Preservatives are required for multidose packaging to prevent microbial contamination. Suitable preservatives include: benzalkonium chloride, thimerosal, chlorobutanol, methyl paraben, propyl paraben, phenylethyl alcohol, edetate disodium, boric acid, sorbic acid, Onamer M, or other agents known to those skilled in the art. Certain modified sarcosinates having the following generic structure are also useful as preservation potentiators in the present invention:

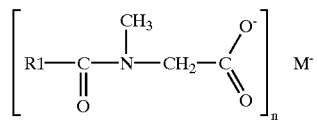

wherein: $R^1 = C_4 - C_{27}$ saturated or unsaturated hydrocarbon:

M=H or a pharmaceutically acceptable salt; and n=1, 2 or 3.

In general, an amount of one or more sarcosinates of this structure are used in the compositions of the present invention in an amount between about 0.005 and about 0.5 percent by weight (wt %), preferably between about 0.01 and about 0.2 wt %. It is most preferred to use between about 0.03 and about 0.12 wt % of one or more of these sarcosinates.

Also preferred are certain lactylates having the following generic structure:

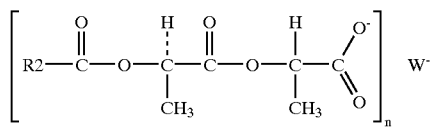

wherein: $R^2 = C_4 - C_{27}$ saturated or unsaturated hydrocarbon;

M=H or a pharmaceutically acceptable salt; and n=1, 2 or 3.

In general, one or more lactylates of this structure may be used in the compositions in an amount between about 0.1 and about 5.0 wt %. It is preferred to use an amount between about 0.1 and 2.0 wt %, and it is most preferred to use about 0.5 wt % of the lactylate.

Preferred surfactants are sold under the Hamposyl® (W. R Grace), Sarkosyl® and Medialan® (Ciba-Geigy) labels. Especially preferred are: lauroyl sarcosine (Hamposyl® L), oleoyl sarcosine (Hamposyl® O), myrstoyl sarcosine (Hamposyl® M), cocoyl sarcosine (Hamposyl® C), stearoyl sarcosine (Hamposyl® S), pelargodoyl sarcosine (Hamposyl® P) and sodium capryl lactylate (Pationic® 122A)

These surfactants can be used in any ophthalmic compositions containing cationic antimicrobials which also contain polyelectrolytes such as high molecular weight, anionic mucomimetic polymers (e.g., carboxyvinyl polymers such as Carbopol®, polystyrene sulfonic acid polymers, cationic exchange resins (e.g., Amberlite® or Dowex®), or the like. Examples of suitable polyelectrolytes are detailed below. Typically such preservatives are employed at a level of from 0.001% to 1.0% by weight.

The tonicity, or osmolality, of the product can be adjusted to either hypotonicity, isotonicity or hypertonicity relative to normal tears by use of conventional materials known to the art. Such tonicity agents, however, are limited to nonionic compounds and typically, when employed, range from 0.00% a to 10% weight percent in the final product. Nonionic agents representatively include: mannitol, dextrose, glycerine and propyleneglycol; their presence in the final product form, however, is optional.

The ophthalmic formulations of the present invention are in the form of. anhydrous salts; pourable, aqueous dispersions; and aqueous gels. The formulations comprise, in addition to conventional ingredients which provide, for example, bacteriostatic and formulatory balance considerations; a polyanionic vehicle, a cationic exchange resin, and the basic active of choice. Such anhydrous salt forms are incorporated into ointments or solid ocular inserts which form colloidal gels in situ on administration to the eye. The pourable liquid and gel embodiments are applied topically to the eye. It should be noted that such liquid and gel embodiments can be obtained from the anhydrous form on formulation with water.

The formulations of the present invention demonstrate sustained release of the basic active and are comfortable on topical administration to the eye. It should be noted, in a general sense, that a stinging sensation results when the basic actives, identified above, are administered neat. Thus, achieving both comfort and sustained release is an unexpected result and permits administration of a class of compounds that otherwise might not be considered.

The compositions are formulated in three basic states: 1.) gels; 2.) pourable liquids, and 3.) anhydrous salts:

1.) Gels: The cationic exchange resin component is dispersed in water. The basic active component is then added with stirring. The polyanionic polymer component is then added. The resulting product has a viscosity ranging from 1000 to 300,000 cps depending on the anionic polymer concentration. The resulting pH is 3.0 to 8.5, which may be adjusted, if necessary, with one of the pH adjusting agents according to the invention, and optionally, HCl.

2.) Pourable Liquids: The cationic exchange resin component is dispersed in 10 to 50 vol. percent of total water taken in formulation, and then basic active is dispersed and/or dissolved with stirrng. The polyanionic polymer, as an aqueous dispersion, is added until the desired pH of the product is obtained. The pH of the product can be adjusted to the desired value by varying basic active/polymer/resin ratio. The final pH of product can be adjusted with addition of the pH adjusting agents according to the invention, and optionally, HCl. The preferred pH range for ophthalmic formulations is from 3.0 to 8.5. The final product is a dispersion, which may require high energy mixing to break any agglomeration to achieve uniformity. Other formulation ingredients are then added with mixing. The resulting product has a viscosity ranging from 1.0 to 20,000 cps depending on the anionic polymer concentration.

3.) Anhydrous Salts: The basic active, the ion exchange resin, and the polyanionic polymer are combined in water, and following mixing, are lyophilized to a powder. Fillers like mannitol and other materials may be added to facilitate the freeze/drying processing according to techniques well known to those skilled in the art. The anhydrous salts produced in this manner can then be formulated or reconstituted to aqueous gels and liquids, or can be formulated and shaped as ocular insets. The lyophilized powder can also be combined with a nonaqueous vehicle to form an ophthalmic ointment. Such anhydrous salt embodiments of the present invention can also be prepared by extracting the initial aqueous dispersion with an organic solvent such as ethanol, chloroform, benzene, or the like, and evaporating the organic solvent to produce the desired salt complex. The resulting product is substantially equivalent to the above-described lyophilized product.

The ophthalmic formulations of the present invention are administered to the eyes as gels, pourable liquids (eye drops), and in the form of ointments and ocular inserts; the latter classifications are formulated form anhydrous salts. All such compositions are formulated to control the release of the basic active upon administration to the eye and thereby provide a sustained release effect. Typically such administration is necessary one to four times, usually one to two per day. The precise dosage regimen is left to the routine discretion of the clinician.

Compositions according to the present invention are further described as follows:

| Component | Specific examples | % |
|---|---|---|
| Active | Betaxolol Hydrochloride | 0.1–5.0% |
| Viscosity agent | Carbopol type polymers, HPMC, HEC, CMC | 0.1–1.0% |
| Ion exchange resin | Poly[styrene(divyl benzene) sulfonic acid | 0.1–5.0% |
| Preservative | Benzalkonium chloride, Polyquad | 0.002–1.0% |
| Tonicity agent | Mannitol | 1.0–5.0% |
| Preservative aid | Boric Acid | 0.001–1.0% |
| Chelating agent | Disodium Edetate | 0–1.0% |
| Perservative | N-lauroylsarcosine | 0–1.0% |
| pH adjusting agent | Tromethamine | to adjust pH, |
| pH adjusting agent | Hydrochloric acid | to adjust pH |
| Solvent | Water | qs 100% |

While the present invention is disclosed generally above, additional embodiments are further discussed and illustrated with reference to the examples below. However, the examples are presented merely to illustrate the invention and are not considered as limitations thereto.

EXAMPLE 1

The compositions shown in Table 1 were prepared as follows: To a solution of levobetaxolol hydrochloride, in purified water was added poly (styrene divinylbenzene) sulfonic acid. The suspension was stirred at which time Carbomer 974P slurry, mannitol, boric acid, disodium edetate and benzalkonium chloride solution were added with continuous stirring. Batch weight was adjusted with purified water and pH was adjusted to 6.5±0.2 with tromethamine. The suspension was autoclaved and then sterile filtered, N-lauroylsarcosine was added aseptically. Formulation batch weight was then brought to 100 ml and final pH was adjusted, as necessary.

TABLE 1

Levobetaxolol Hydrochloride Formulations

| | Concentration | | |
|---|---|---|---|
| Ingredient | 0.25% Percent w/v | 0.5% Percent w/v | 0.75% Percent w/v |
| Levobetaxoiol hydrochloride | 0.28[a] | 0.56[b] | 0.84[c] |
| Poly(styrene divinylbenzene) Sulfonic Acid | 0.375 | 0.75 | 1.125 |
| Carbomer 974 P | 0.35 | 0.35 | 0.35 |
| Mannitol | 4.5 | 4.0 | 3.67 |
| Boric Acid | 0.3 | 0.3 | 0.3 |
| Disodium Edetate | 0.01 | 0.01 | 0.01 |
| Benzalkonium Chloride | 0.01 + 5% excess[d] | 0.01 + 5% excess[d] | 0.01 + 5% excess[d] |
| N-Lauroylsarcosine | 0.03 | 0.03 | 0.03 |
| Tromethamine | pH adjust to 6.5 | pH adjust to 6.5 ± 0.2 | 6.5 ± 0.2 |
| Hydrochloric Acid (if needed) | 6.5 ± 0.2 | 6.5 ± 0.2 | 6.5 ± 0.2 |
| Purified Water | QS 100% | QS 100% | QS 100% |

[a]Equivalent to 0.25% betaxolol free base
[b]Equivalent to 0.5% betaxolol free base
[c]Equivalent to 0.75% betaxolol free base
[d]The 5% excess is added as a development overage

EXAMPLE 2

The results in Table 2 demonstrate that there is an increased bound fraction of betaxolol when TRIS or triethanolamine are utilized to adjust the pH of Betoptic S as measured by HPLC.

TABLE 2

Influence of several pH adjusting bases on bound betaxol in suspension

| pH Adjusting Base | % Bound Betaxolol |
|---|---|
| NaOH (Control) | 56 |
| TRIS | 63 |
| TEA | 59 |
| Na HEPES | 53 |

EXAMPLE 3

The results in Table 3 summarize work done with TRIS vs. NaOH and confirm that the use of TRIS as a pH adjusting agent increases the fraction of betaxolol bound to the resin which in turn increases comfort.

TABLE 3

| Components | 1 | 2 | 3 | 4 | 5 | 6 | 7 | 8* | Betopic-S* |
|---|---|---|---|---|---|---|---|---|---|
| (S) Betaxolol HCl, USP | 0.56% | 0.56% | 0.56% | 0.56% | 0.56% | 0.56% | 0.56% | 0.28% | 0.28% |
| Amberlite IRP-69, NOC | 0.75% | 0.75% | 0.75% | 0.75% | 1.00% | 0.75% | 0.75% | 0.25% | 0.25% |
| Carbomer 974P | 0.40% | 0.40% | 0.40% | 0.40% | 0.40% | 0.40% | 0.40% | 0.45% (934P) | 0.20%** |
| Mannitol, USP | 3.75% | 3.75% | 3.75% | 3.75% | 3.75% | 3.75% | 3.75% | 4.8% | 4.5% |
| Boric acid, NF | 0.30% | 0.30% | 0.40% | 0.40% | 0.40% | 0.40% | 0.40% | 0.4% | 0 |
| Disodium EDTA, USP | 0.01% | 0.01% | 0.01% | 0.01% | 0.01% | 0.01% | 0.01% | 0.01% | 0.01% |
| Benzalkonium Chloride, NF | 0.01% + 5% xs | 0.01% + 5% xs | 0.01% + 5% xs | 0.01% + 5% xs | 0.01% + 5% xs | 0.01% + 5% xs | 0.01% + 5% xs | 0.01% + 5% xs | 0.01% + 5% xs |
| N-Lauroylsarcosine, NOC | 0.03% | 0.03% | 0.03% | 0.03% | 0.03% | 0.03% | 0.03% | 0.03% | 0 |
| Tromethamine, AR 10% Stock | 25 ml | — | 30 ml | — | — | 32.5 ml | — | | |
| NaOH | — | 6N, 3.3 ml | — | 6N, 4.1 ml | 6.25N, 2.85 ml | — | 6.25N, 2.9 ml | NaOH | NaoH |
| Purified Water, OSP | 100% | 100% | 100% | 100% | 100% | 100% | 100% | 100% | 100% |
| Batch Size Made | 200 gm | 200 gm | 200 gm | 200 gm | 200 gm | 200 gm | 200 gm | | |
| pH | 6.5 | 6.5 | 6.6 | 7.0 | 7.0 | 7.0 | 7.0 | 7.0 | 7.6 |
| % Total Betaxolol | 99.86% | 102.82% | 99.66% | 108.92% | 98.11% | 104.23% | 98.41% | 98%, 99% | 95–105 |
| % Free Betaxolol | 20.50% | 24.55% | 21.13% | 27.70% | 21.61% | 23.11% | 28.23% | 45, 46 | 5%–25% |
| Viscosity @ 1.5 RPM; CP 42 | 382, 379 | 301, 294 | 250, 281 | 259, 282 | 111, 109 | 235, 254 | 76.8, 79.5 | 260 (50–100) | NMT 350 @ 1.5 pm |
| Osmolaritry | 283 | 284 | 287 | 307 | 273 | 307 | 290 | 312 | 270–300 |

*R.S.-Betaxolol HCl
**Carbomer 934P

EXAMPLE 4

The results in Table 4 summarize work done with TRIS vs. NaOH and confirm that the use of TRIS as a pH adjusting agent increases the fraction of betaxolol bound to the resin. These results further confirm that the inclusion of TRIS does not modify the preservative properties of the formulations.

In the previous descriptions, numerous specific details are set forth, such as specific materials, structures, chemicals, processes, etc., in order to provide a thorough understanding of the present invention. However, the present invention can be practiced without resorting to the details specifically set forth. In other instances, well known processing structures have not been described in detail in order not to unnecessarily obscure the present invention.

TABLE 4

PET and comfort results of initial three formulation of 0.50% (S)Betaxolol Suspension Formualtion

| Components | 1 | 3 | 4 | 8 | Betoptic ® S |
|---|---|---|---|---|---|
| (S) Betaxolol, HCL, USP | 0.56% | 0.56% | 0.56% | 0.28%* | 0.28%* |
| Amberlite IRP-69, NOC | 0.75% | 0.75% | 0.75% | 0.25% | 0.25% |
| Carbomer 974P | 0.40% | 0.40% | 0.40% | 0.45% (934P) | 0.20% |
| Mannitol, USP | 3.75% | 3.75% | 3.75% | 4.8% | 4.5% |
| Boric acid, NF | 0.30% | 0.40% | 0.40% | 0.4% | 0 |
| Disodium EDTA, USP | 0.01% | 0.01% | 0.01% | 0.01% | 0 |
| N-lauryl sarosine | 0.03 | 0.03 | 0.03 | 0.03 | 0 |
| Benzalkonium Chloride, NF | 0.01% + 5% xs | 0.01% + 5% xs | 0.01% + 5% xs | 0.01% + 5% xs | 0.01% + 5% xs |
| Tromethamine, AR 10% Stock | 25 ml | 30 ml | — | — | |
| NaOH | — | — | 6N, 4.1 ml | NaOH | NaoH |
| Purified Water, USP | 100% | 100% | 100% | 100% | 100% |
| Batch Size Made | 200 gm | 200 gm | 200 gm | — | — |
| pH | 6.5 | 6.6 | 6.5 | 7.0 | 7.6 |
| PET Results | Pass USP Pass Ph. Eur. B | Pass USP Pass Ph. Eur. B | Pass USP Pass Ph. Eur. A | Pass USP Pass Ph. Eur. B | Pass USP |

*Racemic R.S. betazolol HCl

EXAMPLE 5

Tables 5, 6, and 7 summarize preferred formulations of the invention.

TABLE 5

BRINZOLAMIDE/LEVOBETAXOLOL OPTHALMIC SUSPENSION

| COMPONENT | PERCENT W/V % |
|---|---|
| Levobetaxolol Hydrochloride | 0.56[a] |
| Brinzolamide | 1 + 2% excess |
| Amberlite IRP-69 | 0.75 |
| Carbopol 974P | 0.3 |
| Mannitol | 4.0 |
| Boric Acid | 0.4 |
| Disodium Edetate | 0.01 |
| Tyloxapol | 0.025 |
| N-lauroylsarcosine | 0.03 |
| Benzalkomium Chloride | 0.01 |
| Tromethamine | QS pH 6.5 ± 0.2 |
| Purified Water | QS 100 |

[a]Equivalent to 0.5 betaxolol base

TABLE 6

| | FORMULAS | | | | | | |
|---|---|---|---|---|---|---|---|
| COMPONENT | 9 | 10 | 11 | 12 | 13 | 14 | 15 |
| Fluprostenol isopropyl ester | 0.004 | 0.004 | 0.004 | 0.004 | 0.004 | 0.004 | 0.004 |
| Levobetaxolol Hydrochloride | 0.56 | 0.56 | 0.56 | 0.56 | 0.56 | 0.56 | 0.56 |
| HCO-40 | 0.5 | 0.5 | 0.5 | 0.5 | 0.5 | 0.5 | 0.5 |
| Amberlite IRP-69 Poly (styrene divinylbenzene) Sulfonic Acid | 1.0 | 0.75 | 1.0 | 1.0 | 1.0 | 0.75 | 0.75 |
| Carbopol 974P | 0.35 | 0.2 | 0.35 | 0.35 | 0.35 | 0.35 | 0.35 |
| Glycerine | — | 1.8 | — | — | — | 1.0 | — |
| Mannitol | 3.5 | — | 3.3 | 3.3 | 3.3 | — | 3.3 |
| Boric Acid | 0.3 | 0.35 | 0.3 | 0.3 | 0.3 | 0.3 | 0.3 |
| Disodium Edetate | 0.01 | 0.01 | 0.01 | 0.01 | 0.01 | 0.01 | 0.01 |
| Benzalkonium Chloride | 0.015 | 0.01 | 0.015 | 0.015 | — | 0.01 | 0.01 |
| N-lauroylsarcosine | 0.05 | 0.05 | 0.05 | 0.04 | 0.05 | 0.05 | 0.05 |
| Tyloxapol | — | 0.025 | — | — | — | — | — |
| Tromethamine | 0.12 | Adjust pH 6.0 ± 0.2 | Adjust pH 6.0 ± 0.2 | Adjust pH 6.0 ± 0.2 | Adjust pH 6.0 ± 0.2 | Adjust pH 6.0 ± 0.2 | Adjust pH 6.0 ± 0.2 |
| Hydrochloric Acid | Adjust pH 6.0 ± 0.2 | Adjust pH 6.0 ± 0.2 | Adjust pH 6.0 ± 0.2 | Adjust pH 6.0 ± 0.2 | Adjust pH 6.0 ± 0.2 | Adjust pH 6.0 ± 0.2 | Adjust pH 6.0 ± 0.2 |
| Purified Water | QS 100% | QS 100% | QS 100% | QS 100% | QS 100% | QS 100% | QS 100% |

TABLE 7

| | FORMULAS | | | |
|---|---|---|---|---|
| COMPONENT | 16 | 17 | 18 | 19 |
| Fluprostenol isopropyl ester | 0.004 | 0.004 | 0.004 | 0.004 |
| Betaxolol (R,S) Hydrochloride | 0.56 | 0.56 | 0.56 | 0.28 |
| HCO-40 | 0.5 | 0.5 | 0.5 | 0.5 |
| Amberlite IRP -69 Poly (styrene divinylbenzene) Sulfonic Acid | 1.0 | 0.75 | 0.75 | 0.375 |
| Carbopol 974P | 0.35 | 0.35 | 0.35 | 0.35 |
| Mannitol | 3.5 | 3.3 | 3.3 | 3.5 |
| Boric Acid | 0.3 | 0.35 | 0.3 | 0.3 |
| Disodium Edetate | 0.01 | 0.01 | 0.01 | 0.1 |
| Benzalkonium Chloride | 0.015 | 0.015 | 0.015 | 0.01 |
| N-Lauroylsarcosine | 0.05 | 0.05 | 0.05 | 0.05 |
| Tromethamine | Adjust pH to 6.3 ± 0.2 | Adjust pH to 6.0 ± 0.2 | Adjust pH to 6.5 ± 0.2 | Adjust pH to 6.0 ± 0.2 |
| Hydrochloric Acid | Adjust pH to 6.3 ± 0.2 | Adjust pH to 6.0 ± 0.2 | Adjust pH to 6.5 ± 0.2 | Adjust pH to 6.0 ± 0.2 |
| Sodium Hydroxide | — | — | — | — |
| Purified Water | QS 100% | QS 100% | QS 100% | QS 100% |

Only the preferred embodiment of the invention and an example of its versatility are shown and described in the present disclosure. It is to be understood that the invention is capable of use in various other combinations and environments and is capable of changes or modifications within the scope of the inventive concept as expressed herein.

What is claimed is:

1. An ophthalmic composition, comprising:
    a) at least one basic active;
    b) a polyanionic polymer;
    c) an ion exchange resin; and
    d) a pH adjusting agent, wherein said agent is present in an amount sufficient to adjust the pH of the composition to between about 3.5 and about 9.5 and wherein the pH adjusting agent is a basic amine and does not substantially disrupt interaction between the basic active and the ion exchange resin.

2. The composition according to claim 1, wherein the basic active is selected from the group consisting of glaucoma agents, muscarinics, carbonic anhydrase inhibitors, dopaminergic agonists and antagonists, post surgical α-2 agonists, anti-infectives, non-steroidal and steroidal anti-inflammatories, prostaglandins, proteins, growth factors, anti-allergics, beta blockers, and mixtures thereof.

3. The composition according to claim 2, wherein the basic active is a beta blocker.

4. The composition according to claim 3, wherein the beta blocker is levobetaxolol.

5. The composition according to claim 3, wherein the beta blocker is present at a concentration between about 0.1% and about 5.0%.

6. The composition according to claim 1, wherein the pH adjusting agent is selected from the group consisting of ammonia, tromethamine (TRIS or Tris(hydroxymethyl) aminomethan), triethanolamine (TEA), N-2-hydroxyethyl piperazine-N'-2-ethanesulfonic acid (HEPES), and mixtures thereof.

7. The composition according to claim 1, wherein the pH adjusting agent further comprises hydrochloric acid.

8. The composition according to claim 1, wherein
said pH adjusting agent is present in an amount sufficient to adjust the pH of the composition to between about 5 and about 9.

9. The composition according to claim 8, wherein
said pH adjusting agent is present in an amount sufficient to adjust the pH of the composition to between about 6 and about 8.

10. The composition according to claim 9, wherein
said pH adjusting agent is present in an amount sufficient to adjust the pH of the composition to about 6.5.

11. The composition according to claim 1, wherein the composition is in the form of an aqueous gel, a pourable aqueous dispersion, or an anhydrous salt.

12. The composition according to claim 1, further comprising one or more preservatives.

13. The composition according to claim 1, further comprising one or more tonicity agents.

14. An opthalmic composition comprising:
levobetaxolol hydrochloride;
poly(styrene divinylbenzene) sulfonic acid;
carbomer;
mannitol;
boric acid;
disodium edetate;
benzalkonium chloride;
N-lauroylsarcosine; and
tromethamine, and optionally hydrochloric acid, in an amount sufficient to adjust the pH of the composition to between about 6.5.

15. The composition according to claim 1, wherein said basic active comprises betaxolol, and prostaglandin or prostaglandin analog.

16. The composition according to claim 15, wherein said betaxolol is levobetaxolol, and said prostaglandin analog is cloprostenol, fluprostenol, latanoprost, or travoprost.

17. The composition according to claim 15, wherein said prostaglandin analog is travoprost.

18. A method of treating an eye in need thereof, which comprises administering topically to an affected eye, an ophthalmic composition comprising:

a) at least one basic active;

b) a polyanionic polymer;

c) an ion exchange resin; and d) a pH adjusting agent, wherein said agent is present in amount sufficient to adjust the pH of the composition to between about 3.5 and about 9.5; and wherein the pH adjusting agent is a basic amine and does not substantially disrupt interaction between the basic active and the ion exchange resin.

19. The method according to claim 18, wherein the basic active is selected from the group consisting of glaucoma agents, muscarinics, carbonic anhydrase inhibitors, dopaminergic agonists and antagonists, post surgical α-2 agonists, anti-infectives, non-steroidal and steroidal anti-inflammatories, prostaglandins, proteins, growth factors, anti-allergics, beta blockers and mixtures thereof.

20. The method according to claim 1, wherein the basic active is a beta blocker.

21. The method according to claim 20, wherein the beta blocker is levobetaxolol.

22. The method according to claim 20, wherein the beta blocker is present at a concentration between about 0.1% and about 5.0%.

23. The method according to claim 19, wherein the pH adjusting agent is selected from the group consisting of ammonia, tromethamine (TRIS or Tris(hydroxymethyl) aminomethan), triethanolamine (TEA), N-2-hydroxyethylpiperazine-N'-2-ethanesulfonic acid), (HEPES), and mixtures thereof.

24. The method according to claim 18, wherein the pH adjusting agent further comprises hydrochloric acid.

25. The method according to claim 18, wherein
said pH adjusting agent is present in an amount sufficient to adjust the pH of the composition to between about 5 and about 9.

26. The method according to claim 25, wherein
said pH adjusting agent is present in an amount sufficient to adjust the pH of the composition to between about 6 and about 8.

27. The method according to claim 26, wherein
said pH adjusting agent is present in an amount sufficient to adjust the pH of the composition to about 6.5.

28. The method according to claim 19, wherein the composition is in the form of an aqueous gel, a pourable aqueous dispersion, or an anhydrous salt.

29. The method according to claim 19, further comprising one or more preservatives.

30. The method according to claim 19, farther comprising one or more tonicity agents.

31. The method according to claim 19, wherein said basic active comprises betaxolol, and prostaglandin or prostaglandin analog.

32. The method according to claim 33, wherein said betaxolol is levobetaxolol, and said prostaglandin analog is cloprostenol, fluprostenol, latanoprost, or travoprost.

33. The composition according to claim 33, wherein said prostaglandin analog is travoprost.

* * * * *